(12) United States Patent
Stryker et al.

(10) Patent No.: US 8,048,044 B2
(45) Date of Patent: Nov. 1, 2011

(54) DRUG DELIVERY SYSTEM

(75) Inventors: Martin W. Stryker, Kalamazoo, MI (US); Donald M. Engelman, Guilford, CT (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

(21) Appl. No.: 12/189,374

(22) Filed: Aug. 11, 2008

(65) Prior Publication Data

US 2009/0048555 A1 Feb. 19, 2009

Related U.S. Application Data

(60) Provisional application No. 60/955,735, filed on Aug. 14, 2007.

(51) Int. Cl.
- *A61M 35/00* (2006.01)
- *A61M 31/00* (2006.01)
- *A61F 13/00* (2006.01)
- *A61H 1/00* (2006.01)

(52) U.S. Cl. ........ 604/290; 604/500; 604/289; 604/293; 604/305; 601/17

(58) Field of Classification Search ...... 5/621; 604/131, 604/305, 20, 28, 135, 890.1, 289, 93.01, 604/22, 293, 290, 506
See application file for complete search history.

(56) References Cited

U.S. PATENT DOCUMENTS

| | | | |
|---|---|---|---|
| 753,990 A | 3/1904 | Lutje | |
| 1,775,442 A | 9/1930 | Sarason | |
| 2,099,744 A * | 11/1937 | Lohr | 601/17 |
| 2,435,894 A | 2/1948 | Marc-Aurele | |
| 2,970,073 A * | 1/1961 | Prange | 134/1 |
| 3,195,539 A | 7/1965 | Hyman | |
| 3,288,140 A | 11/1966 | McCarthy | |
| 3,315,665 A | 4/1967 | MacLeod | |
| 3,659,600 A * | 5/1972 | Merrill | 604/891.1 |
| 3,712,298 A | 1/1973 | Snowdon et al. | |
| 3,785,374 A | 1/1974 | Lipson | |
| 3,920,006 A | 11/1975 | Lapidus | |
| 4,003,371 A | 1/1977 | Fischer | |
| 4,353,359 A | 10/1982 | Milbauer | |
| 4,376,437 A | 3/1983 | Sundheim et al. | |
| 4,382,441 A | 5/1983 | Svedman | |
| 4,460,370 A | 7/1984 | Allison et al. | |
| 4,509,513 A | 4/1985 | Lasley | |
| 4,620,538 A | 11/1986 | Koegel et al. | |
| 4,624,656 A * | 11/1986 | Clark et al. | 604/23 |
| 4,801,291 A | 1/1989 | Loori | |
| 4,863,457 A | 9/1989 | Lee | |

(Continued)

OTHER PUBLICATIONS

PCT International Search Report mailed Jan. 21, 2009, for corresponding PCT Application No. PCT/US2008/073090.

(Continued)

*Primary Examiner* — Theodore Stigell
*Assistant Examiner* — Bradley Thomas, Jr.
(74) *Attorney, Agent, or Firm* — Warner Norcross & Judd LLP (57) ABSTRACT

A drug delivery system including a chamber, which is configured for enclosing or covering at least a surface of a patient, a source of a drug, and a pressure source, which selectively pressurizes the chamber. In addition, the system includes a controller for controlling the transfer of the drug to the chamber wherein the drug is administered to the surface of the patient under pressure.

18 Claims, 10 Drawing Sheets

U.S. PATENT DOCUMENTS

| | | | |
|---|---|---|---|
| 4,886,489 A * | 12/1989 | Jacobsen et al. | 604/20 |
| 4,953,565 A | 9/1990 | Tachibana et al. | |
| 5,029,579 A | 7/1991 | Trammell | |
| 5,060,644 A | 10/1991 | Loori | |
| 5,152,757 A | 10/1992 | Eriksson | |
| 5,154,697 A | 10/1992 | Loori | |
| 5,176,663 A | 1/1993 | Svedman et al. | |
| 5,228,431 A | 7/1993 | Giarretto | |
| 5,312,385 A | 5/1994 | Greco | |
| 5,358,494 A | 10/1994 | Svedman | |
| 5,447,504 A | 9/1995 | Baker et al. | |
| 5,607,408 A | 3/1997 | Boucly | |
| 5,607,418 A | 3/1997 | Arzbaecher | |
| 5,688,236 A | 11/1997 | Gragg | |
| 5,738,093 A | 4/1998 | Santi | |
| 5,788,682 A | 8/1998 | Maget | |
| 5,795,314 A | 8/1998 | Berenstein | |
| 5,810,795 A | 9/1998 | Westwood | |
| 5,837,281 A * | 11/1998 | Iga et al. | 424/449 |
| 5,848,998 A * | 12/1998 | Marasco, Jr. | 604/290 |
| 5,865,722 A | 2/1999 | Heng | |
| 6,013,094 A | 1/2000 | De Cubber et al. | |
| 6,060,020 A | 5/2000 | Piuk et al. | |
| 6,251,100 B1 * | 6/2001 | Flock et al. | 606/2 |
| 6,398,767 B1 | 6/2002 | Fleischmann | |
| 6,416,293 B1 * | 7/2002 | Bouchard et al. | 417/53 |
| 6,432,077 B1 | 8/2002 | Stenzler | |
| 6,458,109 B1 * | 10/2002 | Henley et al. | 604/304 |
| 6,471,685 B1 | 10/2002 | Johnson | |
| 6,584,971 B1 | 7/2003 | Denyer et al. | |
| 6,635,035 B1 | 10/2003 | Marasco et al. | |
| 6,685,681 B2 | 2/2004 | Lockwood et al. | |
| 6,752,794 B2 | 6/2004 | Lockwood et al. | |
| 6,755,807 B2 | 6/2004 | Risk, Jr. et al. | |
| 6,764,462 B2 | 7/2004 | Risk, Jr. et al. | |
| 6,800,074 B2 | 10/2004 | Henley et al. | |
| 6,810,288 B2 | 10/2004 | Joshi | |
| 6,824,533 B2 | 11/2004 | Risk, Jr. et al. | |
| 6,855,135 B2 | 2/2005 | Lockwood et al. | |
| 6,905,459 B2 | 6/2005 | Humphries, Jr. | |
| 6,951,215 B1 | 10/2005 | Hoffman | |
| 7,022,113 B2 | 4/2006 | Lockwood et al. | |
| 7,195,624 B2 | 3/2007 | Lockwood et al. | |
| 7,216,651 B2 * | 5/2007 | Argenta et al. | 128/897 |
| 2002/0017299 A1 * | 2/2002 | Hickle | 128/204.21 |
| 2002/0160057 A1 | 10/2002 | Park | |
| 2005/0261615 A1 | 11/2005 | Weston | |
| 2006/0185670 A1 | 8/2006 | Loori et al. | |
| 2007/0041960 A1 | 2/2007 | Freeman et al. | |
| 2007/0299369 A1 * | 12/2007 | Babaev | 601/2 |
| 2008/0005840 A1 * | 1/2008 | Zelnik | 5/601 |

OTHER PUBLICATIONS

P. Svedman et al., A Dressing System Providing Fluid Supply and Suction Drainage Used for Continuous or Intermittent Irrigation, Annals of Plastic Surgery, vol. 17, No. 2, Aug. 1986, pp. 125-133.
P. Svedman et al., A Dressing Allowing Continuous Treatment of a Biosurface, IRCS Medical Science: Biomedical Technology; Clinical Medicine; Surgery and Transplantation, vol. 7, Mar. 1979, p. 221.
P. Svedman et al., "Staphylococcal Wound Infection in the Pig: Part I. Course," Ann. Plast. Surg. 23(3):212-218, (Sep. 1989). NPL-684.
P. Svedman, Irrigation Treatment of Leg Ulcers Lancet, 1:532, 1983.

* cited by examiner

DRUG DELIVERY SYSTEM

The present application claims the benefit of U.S. provisional application entitled DRUG DELIVERY SYSTEM, filed Aug. 14, 2007, Ser. No. 60/955,735, which is incorporated by reference in its entirety herein.

FIELD OF THE INVENTION

The present invention relates to a system for delivering drugs and, more specifically, to a drug delivery system that administers drugs through the surface tissue of a patient.

BACKGROUND OF THE INVENTION

Current drug delivery systems include several delivery mechanisms, including transdermal delivery, inhalation, ingestion, injection, nasal delivery, ocular delivery, buccal delivery, and suppository delivery, such as anal or vaginal suppository delivery. While the human skin is an excellent anatomical and biochemical barrier, through-the-skin (TTS) therapy has been used for many years. Due to the impermeability of skin, however, only low molecular weight medications have been used successfully. As a result, delivery of many drugs or medications has been relegated to more conventional methods, and most commonly injections via hypodermic needles, ingestion, or insertion by way of suppositories. Needles, however, break the skin barrier and, hence, may increase the risk of infection and, further, the risk of exposure to health workers to transmission of diseases. Suppositories may not be as successful due to systemic elimination. With oral delivery, the drug may not reach its intended target with the desired concentration. Further, with more medications, such as chemotherapy, having deleterious effects on the body, targeting of a drug has taken on new significance. Accordingly, there is a need for an enhanced drug delivery system that would reduce the reliance on the use of needles, pills or suppositories for delivering medication and, further, that can better target the area to be treated.

SUMMARY OF THE INVENTION

Accordingly, the present invention provides a drug delivery system that can deliver a drug through the surface tissue of a patient, whether the tissue is alive or dead, thus eliminating the various problems associate with, for example, injection, ingestion, or suppositories, and may be used to better target the drug.

In one form of the invention, a drug delivery system is provided that can be used to deliver a drug or drugs through the patient's surface tissue, including skin or tissue below the skin, for example, at a wound bed or surgical incision, while overcoming the transcutaneous transport problem. The drug delivery system of the present invention provides a pressurized chamber, which aids in the delivery of the drugs to increase drug bioavailability. Further, drug delivery may be achieved by delivering the drug in a gas, vapor, or liquid or combinations thereof.

In another form of the invention, a drug delivery system includes a chamber, a source of a drug, a pressure source, and a controller. The chamber is configured for enclosing or covering at least a surface of a patient's body. The controller is in communication with the pressure source to selectively pressurize the chamber and, further, controls the transfer of the drug to the chamber wherein the drug is administered to the surface of the patient under pressure.

In one aspects when the surface of the patient is a skin surface, the drug delivery system may also include a skin poration device, which is used to enlarge the pores of the patient's skin at the surface of the patient to thereby increase the skin's porosity. For example, the skin poration device may comprise an electrical circuit for generating a current or for generating a voltage, which may be applied to the skin surface of the patient. Alternately, the skin poration device may generate an ultrasound wave in the chamber for applying an ultrasound wave to the skin surface of the patient, or generate radiation in the chamber for applying radiation to the skin surface of the patient. For example, the skin poration device may generate heat, electromagnetic radiation, microwave radiation, or RF radiation.

According to another form of the invention, a drug delivery system includes a chamber, a pressure source, a skin poration device, and a controller. The chamber is configured for enclosing or covering at least a skin surface of a patient's body. The controller is in communication with the pressure source to selectively pressurize the chamber wherein a drug applied to skin surface of the patient is administered to the skin surface of the patient under pressure. Further, the skin poration device generates a heat, wave, current, or voltage that is applied to the patient's skin to increase the skin's porosity.

In any of the above inventions, the controller may cycle the pressure between a first pressure and a second pressure, with the first pressure being different than the second pressure. For example, the second pressure may comprise a negative pressure.

In another aspect, each of the systems may include a drug reservoir, with the controller controlling the flow of the drug from the reservoir to the chamber. In yet a further aspect, the systems may also include a source of gas, which is in selective fluid communication with the chamber. Further, the controller may be used to control the fluid communication between the source of gas and the chamber. Optionally, the controller may combine the gas with the drug so that the drug is delivered in a vapor form to the chamber.

According to another aspect, the drug delivery systems may include a humidifier in selective fluid communication with the chamber. For example, the controller may control the fluid communication between the humidifier and the chamber. Again, the controller may combine the humid air with the drug and, further, with the drug and gas mixture.

According to yet another aspect, in any of the drug delivery systems noted above, the system may includes a nebulizer, which produces a spray or mist with the drug. The spray or mist is in fluid communication with the chamber. Again, the controller may control the flow of the spray or mist into the chamber.

In another aspect, the systems may include a thermal regulator, which regulates the temperature of the drug, gas, and/or moisture or mixture thereof flowing into the chamber.

According to yet another aspect, any of the chambers may be formed by a chamber wall that is configured for enclosing at least a portion of a patient's body, such as a patient's head, ear, leg, arm, wrist, chest, groin area, or may enclose substantially, if not, the entire body of the patient.

In a further aspect, the chamber may be configured to form a reservoir for holding a liquid, with the controller directing the flow of the drug into the liquid in the chamber and further pressurizing a portion of the chamber above the liquid, hence pressurizing the liquid.

According to yet another aspect, any of the drug delivery systems described above may be incorporated into a patient support. For example, the system may have a patient-facing opening for facing the patient that is in fluid communication with the chamber, which is provided at the patient support's surface wherein the weight of the patient seals the patient-facing opening against the patient's skin. Optionally, the patient support includes a plurality of the chambers and/or systems for treating several surfaces of the patient's body.

In another form of the invention, a method of delivering a drug to a patient includes providing a chamber, which is configured for enclosing at least a surface of a patient, exposing the patient's surface to a drug in vapor form, and pressurizing the chamber, wherein the drug is administered to the surface of the patient under pressure.

In another form of the invention, a method of delivering a drug to a patient includes providing a chamber, which is configured for enclosing at least a surface of a patient, directing the flow of a drug into the chamber, controlling the flow of the drug in to the chamber, and pressurizing the chamber, wherein the drug is administered to the surface of the patient under pressure.

In any of the above methods, the pressure may be cycled between a first pressure and a second pressure, with the first pressure being different than the second pressure. For example, the pressure may be cycled between a positive pressure and a negative pressure.

In yet another form of the invention, a method of delivering a drug to a patient includes providing a chamber, which is configured for enclosing at least a surface of a patient, applying a drug to a patient's surface, pressurizing the chamber, wherein the drug is administered to the surface of the patient under pressure, and cycling the pressure between two different pressure values.

In another aspect of the above methods, a gas may be directed into the chambers, which may be used to transport the drug, compliment the drug either by enhancing the absorption of the drug, and/or provide additional treatment.

Further, the humidity or temperature in the chambers may be controlled. For example, the humidity or temperature in the chambers may be increased. Optionally, when the drug is delivered to the chambers for application, the drug may be transformed into a spray or mist form and then directed into the chambers.

Accordingly, the present invention provides a drug delivery system that can deliver a drug or drugs through-the-surface-tissue, thus eliminating the various problems associate with, for example, injection, ingestion, or suppositories, and may be used to better target the drug by applying the drug or drugs to a localized surface of the patient.

These and other objects, advantages, purposes, and features of the invention will become more apparent from the study of the following description taken in conjunction with the drawings.

DETAILED DESCRIPTION OF THE INVENTION

Figure 1:
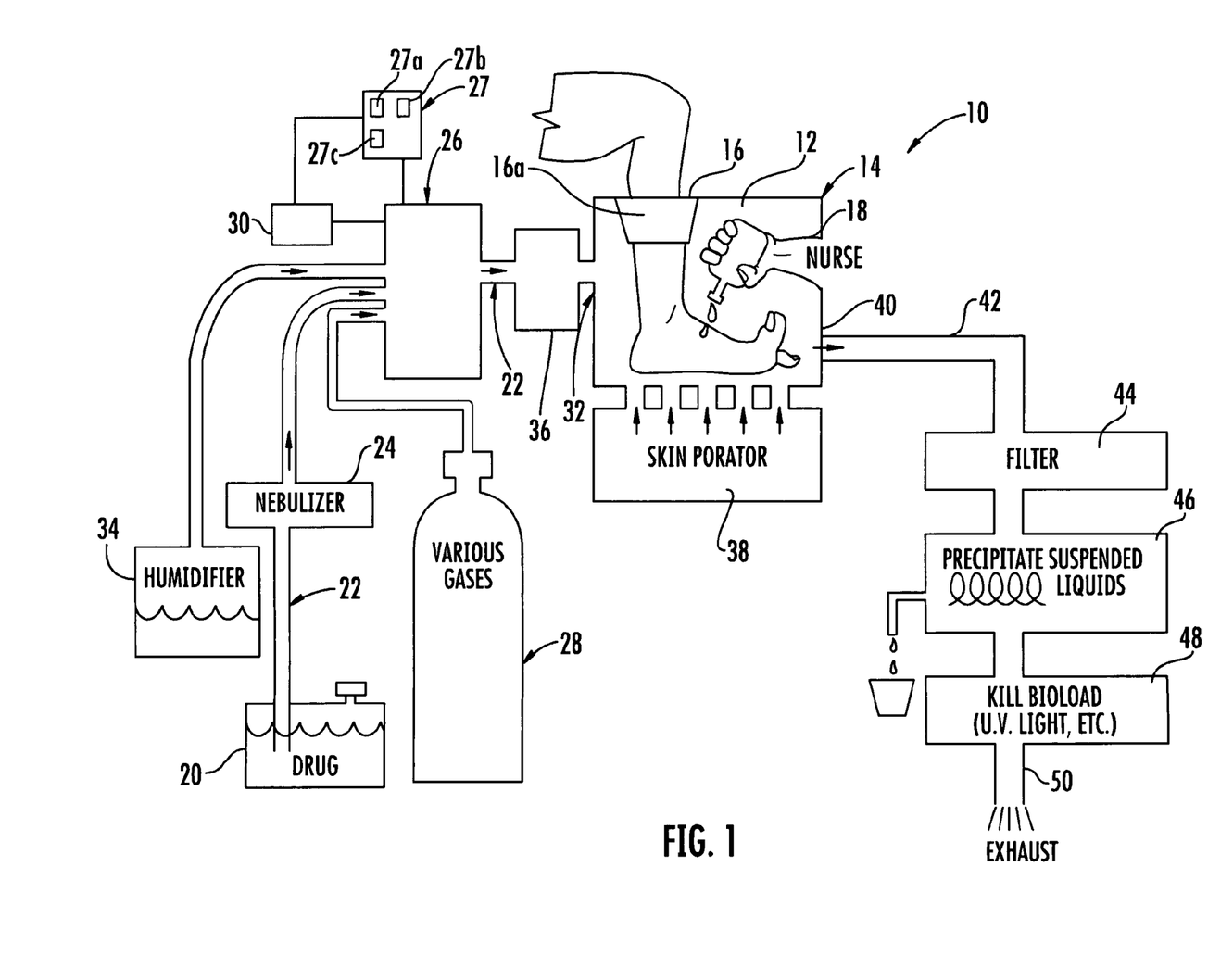
FIG. 1 is a schematic representation of a drug delivery system of the present invention in the form of a vapor system.

Referring to FIG. 1, the numeral 10 generally designates a drug delivery system of the present invention. As will be more fully described below, drug delivery system 10 is a through-the-surface-tissue drug delivery system that delivers a drug or drugs to a body surface, such as the skin surface or tissue, of a patient at elevated pressures to facilitate access of the drug to the tissue. The surface may include a patient's skin, tissue beneath the skin, including a wound bed or surgical site. In addition, the drug may be delivered to the surface using pressure cycling, which further facilitates the entry of the drug into the tissue, whether topically applied prior to treatment in the chamber or applied to the surface in the chamber as a mist, spray, or liquid. Further, in addition to the higher pressure or pressure cycling environment, the tissue may be exposed to a wide range of gases other than air, including inert gases, such as argon, or therapeutic gases, such as oxygen, nitrous oxide, ozone, carbon dioxide, or a mixtures thereof, as well as an anesthetic gas. The gas maybe used to enhance drug delivery and/or provide additional treatment.

While reference is made herein to the term "drug" or "drugs", it should be understood that this term is used broadly to include pharmaceuticals, including pain killers, such as opiates or steroids; hormones, such as androgens and estrogens, peptide hormones such as insulin, as well as performance enhancing drugs, such as steroid hormones; proteins, including morphogenetic proteins, such as bmp-2 and bmp-7; nutrients; antibiotics, such as tetracycline, penicillin, amoxicillin, erythromycin, for example; herbal medicine; vitamins; or other treatments. Further, when using the term "drug" or "drugs" it should be understood that this also includes any carriers, such as solvents or excipients, which may be added to the drug to aid in the delivery of the drug as well as enhance penetration or efficacy of the drug.

As best seen in FIG. 1, drug delivery system 10 includes a chamber 12. The size and configuration of the chamber may vary greatly depending on the application. For example, in the illustrated embodiment chamber 12 is enclosed by a housing or chamber walls 14 and includes an access port 16 in one of the chamber walls to allow an appendage, such as a foot, to be inserted into chamber 12. Further the shape may be varied; for example, although illustrated as having a box configuration, the chamber walls may be configured as a cylinder or another closed shape or a half-dome that seals against a surface, such as a patient support surface. Suitable materials for the chamber wall include polymers, including reinforced polymers, which can be molded into the desired shape or assembled from polymer components, such as polymer panels, which are then secured together by fasteners or clamps or welds or the like, such as described in U.S. Pat. No. 5,061,644, which is incorporated by reference herein in its entirety. Chamber 12 may also be formed by an inflatable chamber wall, such as disclosed in U.S. Pub. No. U.S. 2006/0185670, which is incorporated by reference herein in its entirety.

Chamber 12 is optimally a sealed chamber so that the chamber may be pressurized and the pressure more easily regulated. In order to seal access port 16, access port 16 includes a sealing member 16a, such as a flexible boot or cuff or the like, to seal the space between the chamber wall and the patient's appendage when the chamber is in use. For example, in addition to providing a seal, an inflatable cuff may reduce or minimize contact with the appendage that is being inserted into the chamber. This is particularly desirable when dealing with treatment of an injured appendage or an appendage with a wound, including a surgical site.

In addition, a second port 18 may be provided to allow access into the chamber by a health worker. For example, port 18 may allow a health worker to topically apply a drug to the patient or to simply position the appendage in the chamber. As noted above, the drug may be in the form of a liquid, such as a lotion or the like, that may be topically applied to the appendage either before the appendage is placed in the chamber or after the appendage is placed in the chamber. After port 18 is used, port 18 is preferably closed, for example, by a door, a boot, or a flange or the like so that port 18 may then be fully sealed.

Example 1

A black, water soluble dye was placed on non-living pig's foot skin and on non-living pig's flesh (no skin). Without pressure the dye just pooled on the surface. With pressure, significant penetration was achieved on both the skin and open flesh. For the pressure test, a portion of a pig's flesh and a portion of a pig's foot skin were placed in a humidified pressure chamber. One drop of black, water soluble food dye was applied to each of the pig's flesh and pig's foot skin in the humidified pressure chamber. The chamber was pressurized to 0.88 psi for five minutes then allowed to return to ambient pressure for one minute. This pressurization in the chamber was repeated ten time equaling a total time of pressurization of one hour. The pig's tissue and foot skin was frozen and sawed open to take the measurements and measured using a digital micrometer. For the skin, the penetration was measured to be about 0.072 inches, and for the flesh, the penetration was measured to be about 0.129 inches.

Alternately, as noted above, the drug may be delivered to chamber 12. As best seen in FIG. 1, system 10 may include a drug supply 20, such as a drug reservoir, that is in fluid communication with chamber 12 through a conduit 22. Though not illustrated, it should be understood that the reservoir may deliver the drug to the chamber under the force of gravity or by way of a pump (not shown). Optionally, the drug or drugs are transformed into a mist or spray form, for example by a nebulizer 24, to facilitate delivery of a dispersed form of the drug into chamber 12 and/or to facilitate mixing with a gas or gases more fully described below.

The flow of the drug from reservoir 20 and through the nebulizer 24 may be controlled by a controller 26. For example, a suitable controller comprises a flow control valve, such as an electrically operated solenoid valve, which can be powered by a circuit with an on/off switch or the like or may be controlled by a control system 27. Control system 27 includes a central processor 27a and an optional memory device 27b. In addition, the control system may include a user input device 27c, such as a keyboard, touch pad or touch screen, to allow a user to input operational parameters, such as the treatment time or duration, the magnitude of the pressure, and/or the treatment cycle time, into the control system or to select pre-selected programs or functions into the control system, which are stored, for example, in memory device 27c. In this manner, system 10 may provide a controlled flow of the drug into the chamber. Furthermore, by introducing the drug in the form of a spray or mist, the drug may be delivered in a form that further facilitates absorption of the drug through the tissue of the patient.

In addition, as noted above, the drug may be combined or mixed with a gas supplied by a source of gas 28, including an inert gas, such as argon, or a therapeutic gas, such as oxygen, including hyperbaric oxygen, nitrous oxide, ozone, carbon dioxide, or an anesthetic gas, or the like, which is also in selective communication with chamber 12 through controller 26. The gas may facilitate the delivery of the drug to the patient's tissue by providing a medium to transport the drug into the chamber and, further, may provide additional therapy, including inhibiting microbial growth. For example, oxygen may inhibit most anaerobes, enhancing leukocyte and macrophage activity and possibly potentiating the effects of antibiotics. Thus, when oxygen is combined with a drug, including antibiotics or nutrients or the like, the effects of the drug may be enhanced in the presence of oxygen. In wound healing, hypoxia arises from disruption of the normal supply of oxygen by the blood. When oxygen is limited, tissues use a form of anaerobic metabolism that produces acid, and the more limited energy available in anaerobic metabolism limits cell growth and tissue repair. Providing oxygen to the tissue by exposing the injured tissue to an increased partial pressure of oxygen is a way to help get the needed oxygen to the cells, so that normal growth and repair can occur. Pressure cycling should facilitate the access of the gas to the tissue, and hence may provide improvement over static pressure. Further, when pulsed pressure, described more fully below, is combined with exposure to a drug the transdermal delivery may be enhanced.

For example, as noted above, central processor 27a may include memory device 27b, which may store a software program that is designed to offer pre-selected treatment regimes and which controls the amount of drug that is delivered to chamber 12, including controlling the period of time that the drug is administered and the amount of drug that is administered. Additionally, when combined with a gas or gases, the software program may control the amount of gas that is delivered with the drug to control the concentration of the drug in the resulting vapor. Optionally, each input (drug, gas, moisture, (described below), and heat (also described below)) may be regulated by providing a separate valve for each input or by providing a valve manifold with inlets for each input. Therefore, controller 26 may control the flow of a drug or drugs, gas, moisture, and heat independently.

As noted above, chamber 12 is optimally a sealed chamber, which may be pressurized to enhance the through-the-surface-tissue delivery of the drug to the patient. Referring again to FIG. 1, chamber wall 14 includes a sealed inlet port 32 through which conduit 22 directs the flow of drugs, gasses, and/or moisture into chamber 12. In addition to controlling the amount of the drug or drugs, gases, and/or moisture that is delivered to the chamber, control system 27 is in fluid communication with a pressure source 30 to thereby control the pressure in chamber 12. Optionally, control system 27 cycles the pressure in chamber 12, for example to provide intermittent pressurization, to facilitate the entry of the drug through-the-surface-tissue into the patient. The use of pressure cycling is believed to facilitate the entry of topically applied liquids. As noted, in the present application such liquids include, drugs, such as antibiotics, painkillers, hormones, or nutrients or the like, which may be accompanied by a gas, such as oxygen. Since restriction of circulation in damaged tissue alters the delivery of gasses and/or nutrients (including glucose) and also limits the removal of waste products, combining the pressure cycling with a liquid might provide added benefits. For example, control system 27 may cycle the pressure in chamber 12 between a first pressure and a second pressure, wherein the second pressure is different than the first pressure. The second pressure may comprise a lower pressure than the first pressure, including a negative pressure, so that the treatment may include cycling between a positive pressure and a negative pressure or between a first negative pressure and a second negative pressure that is greater or less than the first negative pressure. As used herein, the terms "positive pressure" and "negative pressure" are defined as greater and less than 1 Atm, respectively.

Further, the duration of the each cycle may be varied. For example, in one treatment option, the pressure may be cycled between two pressure values over the same period of time—that is the first pressure may be applied for a period of time having a duration of time T1, with a second pressure applied for a second period of time having the same length of time T1. Alternately, the first pressure may be applied for a different length of time than the second pressure. For example, the first pressure may be applied for a period of time having a duration of T1, while the second pressure may be applied for a period of time having a duration of time T2, where T2 is greater than or less than T1. This process may be repeated or may be varied further. For example, a third pressure may be applied for another period of time, which is greater or lesser than either the first two pressures and for a longer or shorter period of time than either of the first or second pressure periods, T1 or T2. While gradual transitions between the pressures may be used, an optimal pressure graph has at least approximately a step function in order to achieve the greatest pumping action at the cell level.

Further, as noted above, energy may be applied to the tissue of the patient being administered using the drug delivery system to heat the tissue to either increase the pores, noted above, or to heat the tissue to cause perspiration. For example, heat may be applied to increase the temperature of the patient's tissue, such as the patient's skin, in combination with the drug delivery step or simply in combination with the pressure, including a vacuum pressure, which may enhance the patient's elimination of toxins through perspiration.

The cycling periods may be controlled by control system 27 and, further, as noted above may be input directly by user interface device 27c, such as a keypad, touch pad or a touch screen, which allows a healthcare giver to administer the treatment based on parameters that are provided to the healthcare worker independent of any stored parameters in the controller. It is believed that pressure cycling facilitates entry of the gas, in part by compression and expansion of the tissue.

Optionally, chamber 12 may be humidified, for example, by directing moisture into chamber 12 from a humidifier 34. Again, the humid air may be directly delivered to chamber 12 from humidifier or may be mixed with the drug and/or gasses in conduit 22 prior to entering chamber 12. With an increased level of humidity in chamber 12, the absorption of some drugs may be enhanced or may simply provide a more comfortable environment for the patient's appendage.

Similarly, a temperature controller 36 may be provided, which increases or decreases or maintains the temperature of the drugs, gasses, and/or moist air mixture that is directed to chamber 12. Again, the heating or cooling of the drugs, gasses, and/or moist air mixture may enhance the drug bioavailability and drug delivery. For example, when treating a patient's skin, the pores of the patient's skin may be enlarged through an increased temperature.

In addition, to enhance the absorption of the drug and/or gasses into the skin, chamber 12 may include a skin poration device 38—that is a device or process that enlarges the pore of the patient's skin by applying energy waves, ultrasonic waves, current or voltage to the skin directly. For example, a suitable skin poration device may include a circuit that generates an electrical current or voltage, which when applied to the patient's skin enlarges the pores. Alternately, the circuit may generate an ultrasound wave in the chamber, which is directed to the patient's skin, which also may enlarge the patient's pores. Alternately, the circuit may generate energy waves in the form of radiation, including magnetic radiation, microwave radiation, and/or radiofrequency radiation, in the chamber which is applied to the patient's skin to thereby enlarge the pores of the patient's skin. The skin poration device may be integrated into chamber 12 or may be provided in a separate housing that is in communication with chamber 12, such as illustrated in FIG. 1.

After treatment, or optionally even during treatment, the waste and/or gas discharge from chamber 12 is exhausted from chamber 12 through an outlet port 40 and is directed through a conduit 42 through a filter 44, which filters any solids that are suspended in the gas discharge. Thereafter, the filtered discharge is passed through a precipitator 46, which precipitates any suspended liquids in the discharge. The balance of the discharge is then directed to a cleaner 48, such as a UV light or incinerator, which kills or destroys a substantial, if not all, the bio-load in the discharge. After the bio-load is substantially removed, the remaining discharge is exhausted to the air through a vent 50. Optionally, the system may include a deodorizer to minimize any odors that may be discharged despite the filtering and destruction of the bio-load.

To further facilitate the delivery of the drug, the drug may be suspended in a carrier, such as a lipid based drug carrier or other liquids, such as solvents or excipients, which will also facilitate drug delivery. Further, the drugs may be applied in concentrated form, for example when directly to the tissue as noted above. In addition, a patient may take a vasodilator, orally for example, which may facilitate the circulation of the patient's capillaries in the vicinity of the application, while a second drug may be applied to the tissue using the through-the-surface-tissue drug delivery system of the present invention. Therefore, it should be understood that the present invention may be used in combination with conventional treatment methods.

As noted above, the present drug delivery system may be used to minimize drug interaction between two or more drugs. For example, one drug may be administered orally, as noted above, or injected (or through a suppository, e.g.), while a second drug may administered using the drug delivery system of the present invention. In addition, as will be more fully described below, specific regions of the patient's body may be targeted for drug treatment. Therefore, the drug system may be used to administer more than one drug, with a third drug administered using the drug delivery system of the present invention that targets a specific region of the patient's body.

Figure 2:
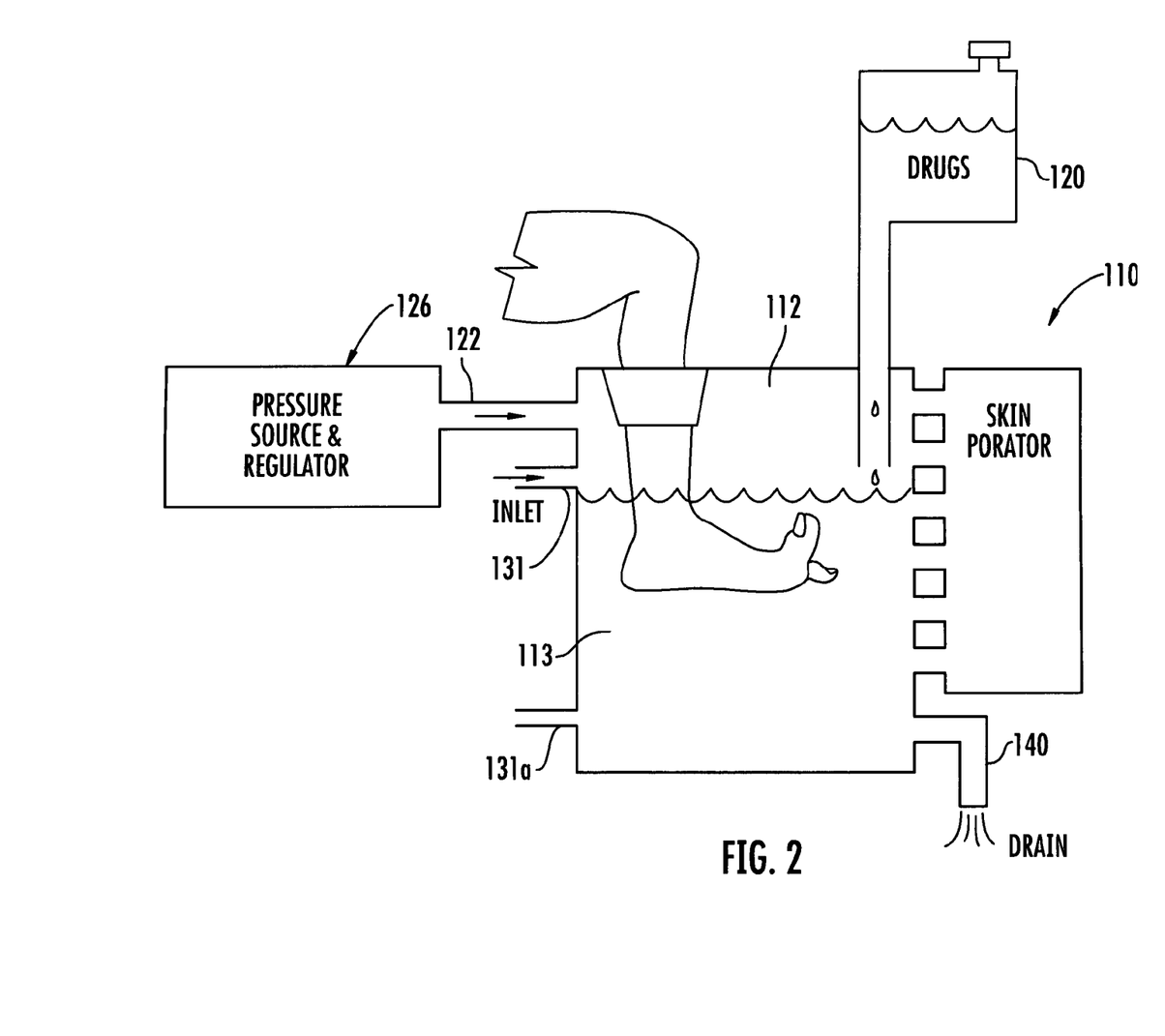
FIG. 2 is a schematic drawing of the drug delivery system of the present invention in the form of a liquid system.

Referring to FIG. 2, the numeral 110 generally designates another embodiment of the drug delivery system of the present invention. Drug delivery system 110 similarly provides a pressurized chamber 112 to enhance absorption of a drug to through a patient's tissue. In the illustrated embodiment, drug delivery system 110 comprises a liquid system in which the appendage is at least partially immersed in a fluid 113, which is contained in chamber 112. For example, a suitable liquid includes water or may include perfluorocarbons, which hold a greater amount of oxygen than water. Hence, the liquid may also be used to apply oxygen to the patient's tissue. Similar to the previous embodiment, the region above the fluid in chamber 112 is pressurized by a pressure source and controller 126. For details of other suitable components and a suitable control system and pressure cycling reference is made to the previous embodiment.

The drugs may be stored in a reservoir 120 similar to the previous embodiment and delivered into chamber 112 and, further, into liquid 113 contained in chamber 112. The flow of the drug from reservoir 120 may similarly controlled by a control system; such as described above. In this manner, chamber 112 provides pressurized air over a drug suspended in a liquid. Optionally, as in the case of the previous embodiment, system 110 may include a temperature controller to heat the liquid and a skin poration device, which applies energy to skin of the patient in the form of energy waves, sound waves, voltage or current to enlarge the pores of the patient's skin and thereby facilitate absorption of the drug through the surface tissue. Further, the liquid in chamber 112 may be circulated to facilitate the mixing of the drugs in liquid and, further, in the case of wound treatment provide debridement of the wound. For example, the liquid the liquid 113 may be circulated in chamber 112 by continually flushing the liquid in the chamber, by continuously filling the chamber through inlet 131 and draining the liquid through the drain outlet 140. Alternately, liquid 113 may be circulated by air or gas injected into the fluid through a second inlet port, for example inlet port 131*a*, which allows air to be injected into liquid 113 while restricting the flow of liquid 113 out of chamber 112.

The discharge from chamber 112 may also be filtered, precipitated and then cleansed by UV radiation, for example, similar to the previous embodiment. Therefore, for further details regarding the discharge reference is again made to the previous embodiment.

Figure 3:
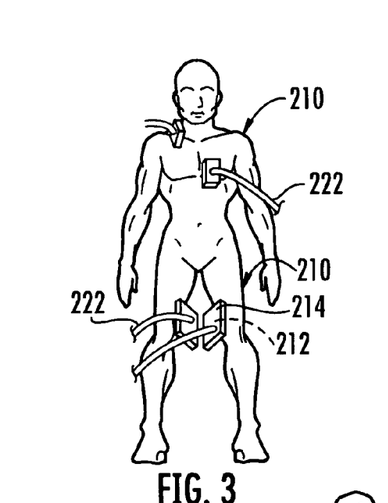
FIG. 3 is a schematic drawing of the drug delivery system of the present invention in the form of topical chambers applied to a patient's body in close proximity with large veins and/or arteries to provide enhanced speed of delivery of the drug.

Referring to FIG. 3, the numeral 210 designates another embodiment of the drug delivery system of the present invention. Drug delivery system 210 incorporates the chamber 212 into a flexible wound cover 214 that is optimally sufficiently flexible to conform to the patient's body. Further, the cover is configured to seal against the patient's skin so that the chamber may be pressurized through as conduit 222 in the same or similar manner described in reference to the first embodiment. In this manner, the wound cover of system 210 is applied to the patient's skin to thereby provide localized treatment of the patient's tissue. For examples of suitable topical wound covers or devices that may be used in conjunction with the present system, reference is made herein to U.S. Pat. Nos. 4,624,656; 5,154,697; and 4,801,291, which are incorporated by reference herein in their entireties. Additionally, the wound cover may be stored at a patient support surface and may comprise, for example, a disposable wound cover, such as described in U.S. Utility Pat. Application entitled PATIENT SUPPORT WITH UNIVERSAL ENERGY SUPPLY SYSTEM, filed Mar. 28, 2008, Ser. No. 12/057,941, which is commonly assigned to Stryker Corporation of Kalamazoo, Mich. and which is incorporated by reference herein in its entirety. Further, the drug or drugs may be delivered to the wound cover using the universal energy supply system described in the above referenced application. It should be understood that for any of the chambers described herein, the chamber may be supplied fluid from the universal energy supply system described in the above referenced application.

As best seen in FIG. 3, topical drug delivery systems 210 may be located at one or more locations at the body, for example at or near large arteries to increase transmission of the drug into the patient's circulatory system. For example, drug delivery systems 210 may be located at the carotoid artery, subclavian artery, or femoral artery. Furthermore, it should be understood that multiple drug delivery systems may be used to treat multiple locations of the patient in order to increase the transmission of drug into the patient's circulatory system from multiple locations. Each system 210 may be individually controlled and further may apply different drugs to each location of the patient's body. Alternately, system 210 may be controlled by a common control system.

It should be understood that the chamber of the present invention may be configured to treat various appendages of the patient and various areas of the patient. For example, referring to FIG. 4, drug delivery system 310 includes a housing 314 and chamber 312 that are configured to treat a wrist of a patient. For example, chamber 312 is configured and located about the wrist to facilitate drug delivery to the veins of the patient's wrist. Again, the drug, gas and/or moisture may be directed into chamber 312 via conduit 322. Further, the discharge is exhausted through outlet port 340, which also may be filtered, precipitated, and cleaned similar to the first embodiment.

Figure 4:
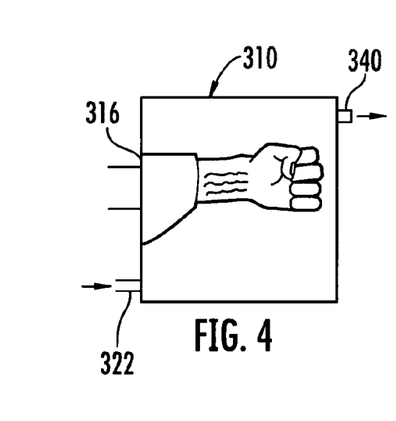
FIG. 4 illustrates a chamber of the drug delivery system of the present invention adapted to deliver a drug to an appendage of the patient, which in the illustrated embodiment comprises a wrist of a patient.

In the illustrated embodiment, an access port 316 to allow a patient's wrist to be inserted into chamber 312 is provided in the side of the chamber, though it should be understood that the access port may be located on the top wall of the chamber as well. Further, port 316 is provided with a boot or sleeve or pressure cuff to seal chamber 312.

Figure 5:
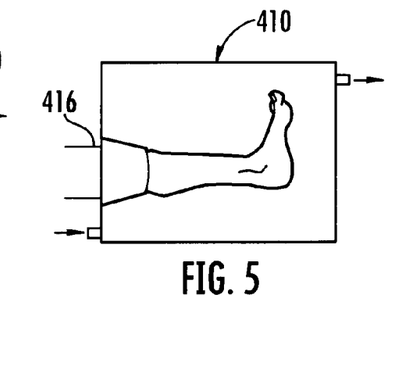
FIG. 5 is a similar view to FIG. 4 illustrating the chamber accommodating a foot of a patient.

Alternately, as seen in FIG. 5, drug delivery system 410 may include a housing 414 and chamber 412 that are configured to receive a leg similar to housings 14 and 114 and chambers 12 and 112. Housing 414 and chamber 412 are, however, configured for use with a patient support surface, such as a bed, and, therefore, provides insertion port 416 on the side of the chamber similar to housing 314. Furthermore, any of the housings and chambers of the present invention may be configured to treat multiple appendages, such as shown in FIG. 6.

Figure 6:
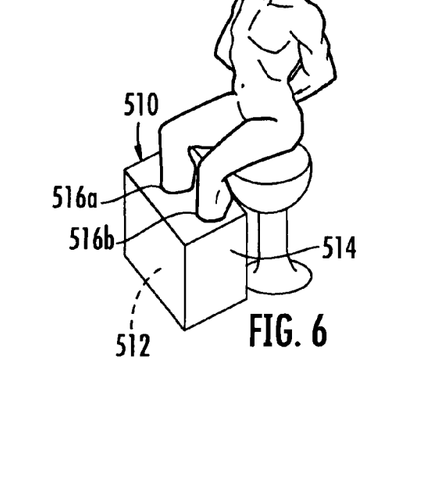
FIG. 6 illustrates another embodiment of a chamber of the drug delivery system of the present invention configured to deliver a drug to two extremities.

As best seen in FIG. 6, drug delivery system 510 includes a housing 514 with pair of ports 516a and 516b, with each configured to receive a leg of a patient, for example. Optionally, ports 516a and 516b are in communication with a common chamber 512. Alternately, each port may be associated with its own chamber; thus, the drug delivery systems of the present invention may include multiple chambers for multiple treatment sites, which allows for different treatment for each site.

Figure 7:
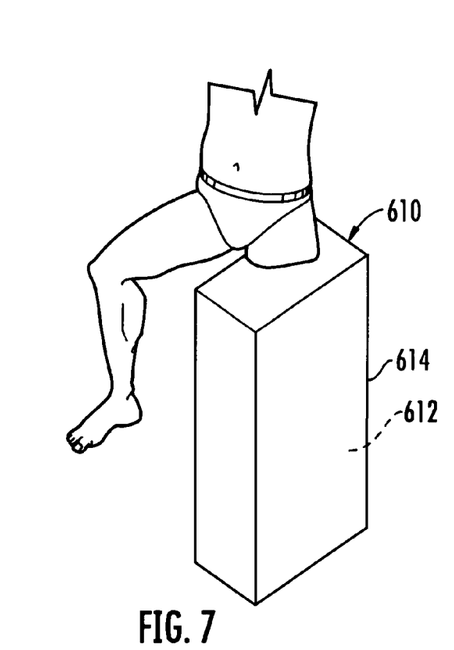
FIG. 7 illustrates another embodiment of the chamber of the present invention configured to enclose a leg of a patient.
Figure 8:
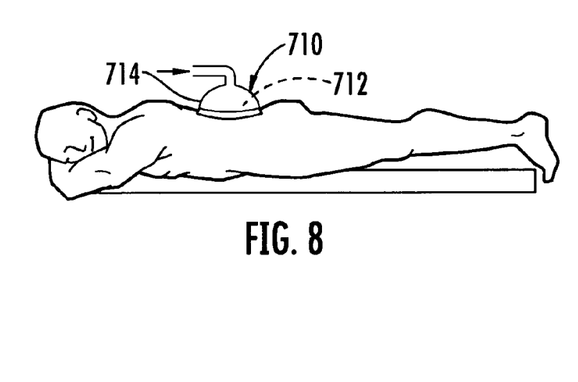
FIG. 8 is a schematic drawing of a chamber of the present invention configured as a topical chamber that may be used, for example, to deliver a drug, such as a steroid, to a patient's back to relieve back pain.

As noted above the size and shape of the chambers may be varied. Referring to FIG. 7, drug delivery system 610 includes a housing 614 and chamber 612 configured to receive an entire leg of a patient. Other areas of the body, which may be treated with the chamber of the present invention, include the spine, such as shown in FIG. 8. As best seen in FIG. 8, the numeral 710 designates another topical version of the drug delivery system of the present invention, which includes a housing 714 and chamber 712 that are configured for treating the back or spine of the patient. For example, chamber 712 may be used to deliver drugs, such as a painkiller, for example a steroid, to relieve back pain.

Figures 9, 10:
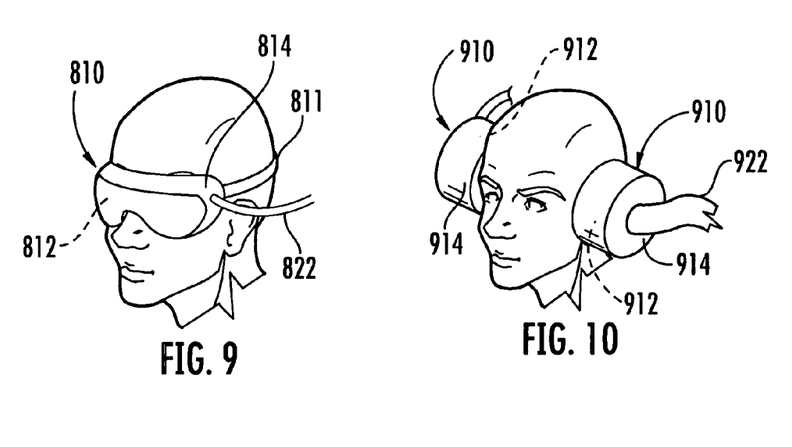
FIG. 9 is a schematic drawing of yet another embodiment of the chamber of the present invention configured for delivering a drug to an eye or eyes of a patient.
FIG. 10 is another schematic drawing of yet another embodiment of the chamber of the present invention, which is configured to enclose an ear of a patient for delivering a drug to the ear.

Referring to FIGS. 9 and 10, the drug delivery system housings and chambers of the present invention may be configured to treat a uniquely-shaped area or a portion of the body. For example referring to FIG. 9, system 810 includes housing 814 and chamber 812 that are configured to cover and enclose one or more eyes of the patient to thereby deliver drug treatment to the skin surrounding the eyes or to deliver a drug to the eyes for treatment of the eyes. In the illustrated embodiment, housing 814 is configured as a goggle-shaped cover that covers both eyes and, further, includes a strap 811 for securing chamber 812 to the head of a patient. As noted previously in reference to the previous embodiments, the drug may be applied topically to the patient's skin or eyes or may be delivered through a conduit 822, which similarly pressurizes the chamber 812, which is positioned over the eye region of the patient.

Referring to FIG. 10, housing 914 and chamber 912 of drug delivery system 910 may be configured for treating an ear of a patient. As best seen in FIG. 10, housings 914 and chambers 912 are configured to be placed over the ears of a patient and, further, seal against the skin of the patient's head around the ear to form relatively airtight chambers 912, which are positioned over the ears. Similarly, each drug delivery system 910 includes a conduit 922 for delivering a drug (and/or a gas and/or moisture) to its respective chamber 912 to treat the ear or to enhance post operative healing. Chamber 912 is similarly pressurized through air or a gas delivered through conduit 922.

Figure 11:
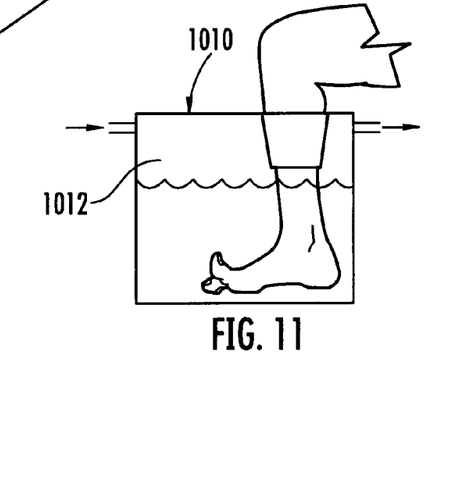
FIG. 11 is a schematic drawing of yet another embodiment of the chamber of the present invention that includes a reservoir with pressurized air over the liquid contained in the reservoir for treating a foot of a patient.
Figure 12:
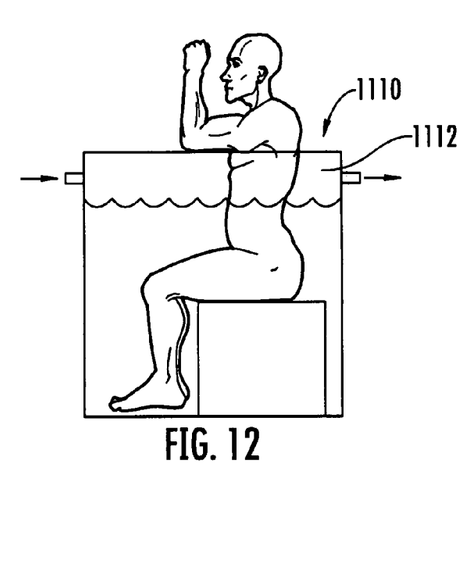
FIG. 12 is a schematic drawing of a partial body chamber of the present invention.
Figure 13:
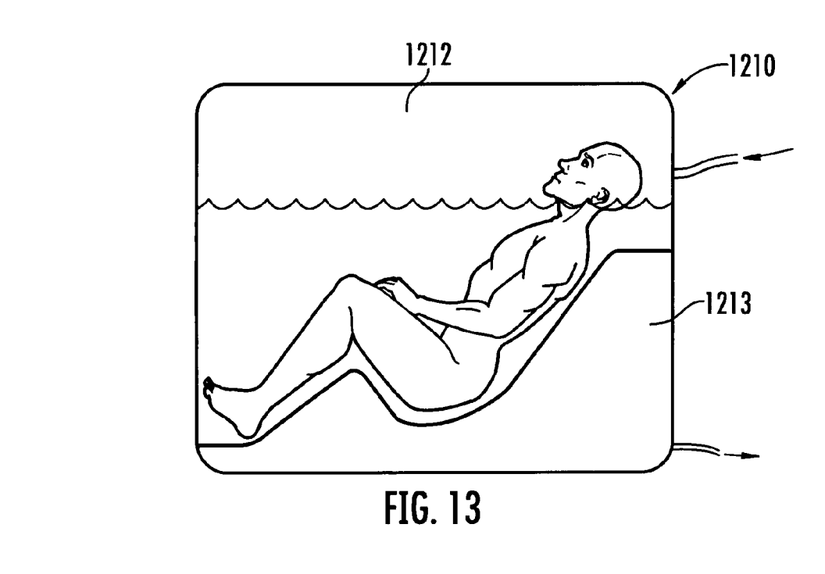
FIG. 13 is a schematic drawing of a total body chamber of the present invention.

Referring to FIGS. 11, 12, and 13, the chambers of the drug delivery systems 1010, 1110, and 1210 of the present invention, may be configured to treat a part of an extremity, such as shown in FIG. 11, or a portion of the patient's body, including the lower portion of the patient's body such as shown in FIG. 12 or almost the entire body of a patient, such as shown in FIG. 13. Again, chambers 1012, 1112, and 1212 provide pressurized air over medication or drug suspended in a liquid.

With reference to system 1210, the total body of a patient may be immersed in chamber 1212 and may optionally form a sensory deprivation chamber with high breathable oxygen content and medication delivered to the patient via the liquid 1213, such as water or perafluorocarbons. Perafluorocarbons carry oxygen so well that a person may in theory be immersed in perafluorocarbon and still breathe.

Figure 14:
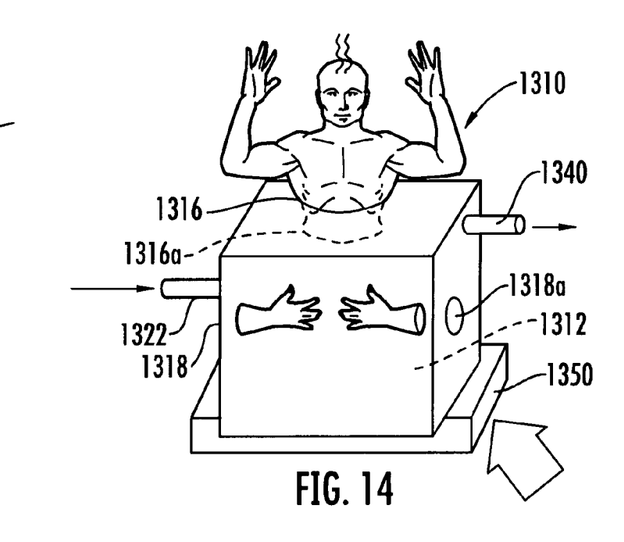
FIG. 14 is a schematic drawing of a chamber for holding an infant or toddler for delivering one or more drugs or medications to the patient with an optional weigh scale system to determine and monitor drug dosage.

Referring to FIG. 14, drug delivery system 1310 may be configured to treat an infant or toddler. For example, the housing 1314 may include an insertion port 1316 for receiving an appendage or portion of the infant's or toddler's body. Multiple access ports 1318a and 1318b may be provided to facilitate a healthcare worker's access to the chamber 1312 as well as to the child supported in chamber 1312. Similar to the first embodiment, these access ports are preferably sealable after use so that chamber 1312 can be pressurized.

In the illustrated embodiment, chamber 1312 is configured to comprise a partial body chamber with the child or infant suspended at the insertion port 1316 by, for example (not shown) a harness or the like. Alternately, the sleeve 1316a that forms the seal between the infant's body and the chamber may be configured as a harness to thereby suspend the child in the chamber 1312. Optionally, chamber 1312 may be placed on a weigh scale system 1350 to determine monitored drug dosage. In this manner, an infant or toddler may be treated with multiple drugs with no painful injection.

Figure 15:
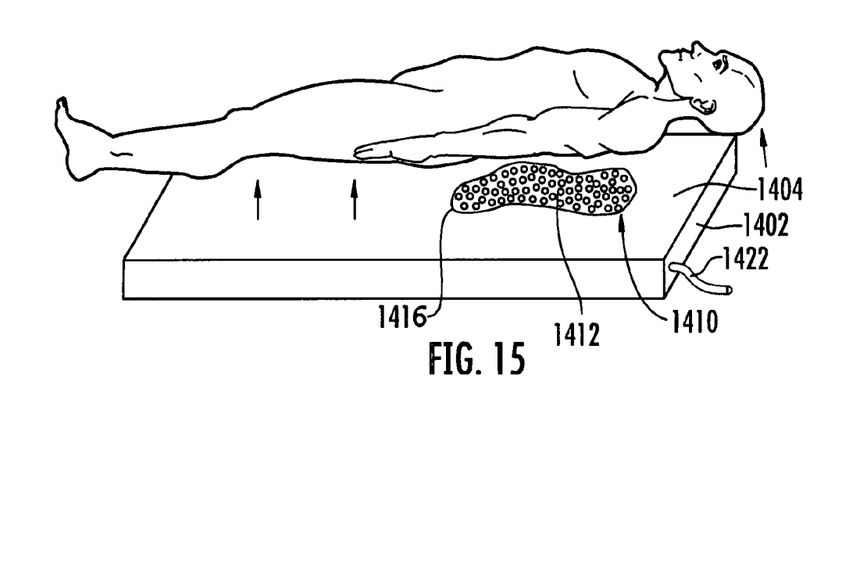
FIG. 15 is a patient support that incorporates a chamber of the drug delivery system of the present invention.
Figure 15A:
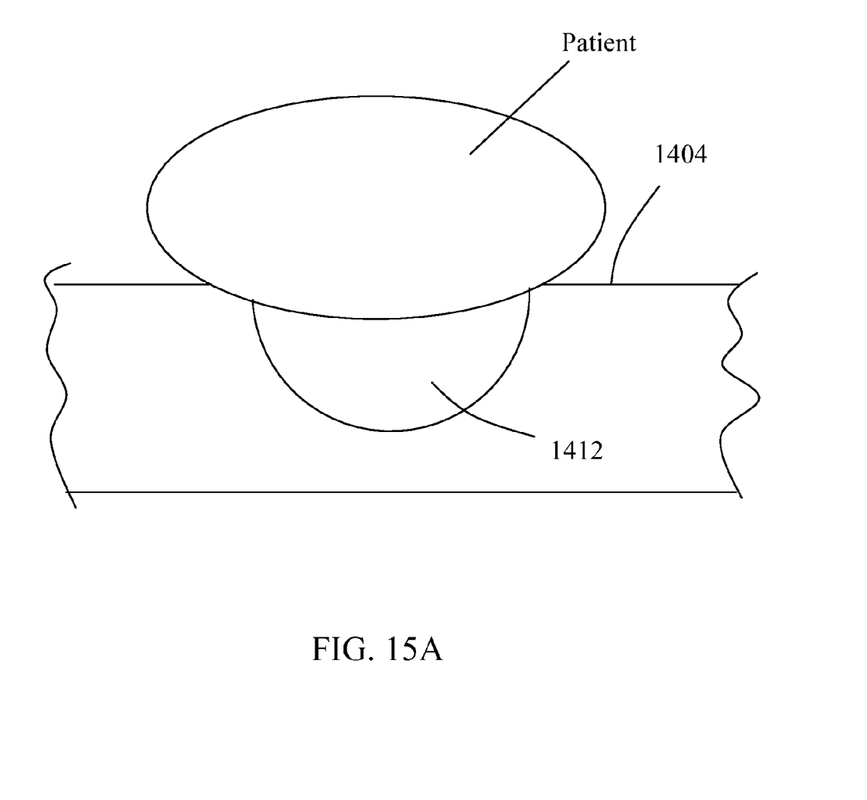
FIG. 15A is a schematic cross-section view illustrating the patient resting on the patient support surface of FIG. 15.
Figure 16:
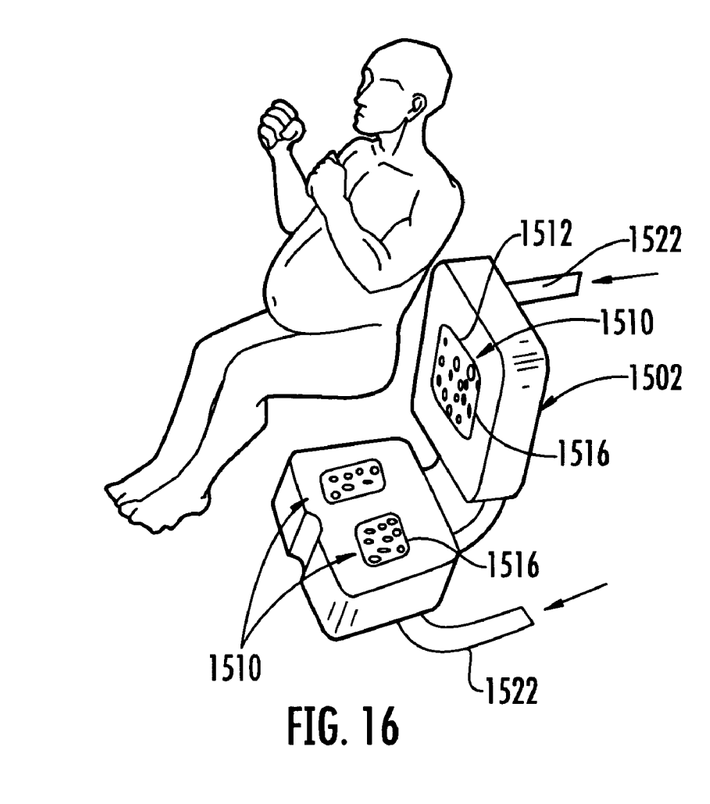
FIG. 16 is another embodiment of a patient support incorporating a plurality of chambers of the drug delivery system of the present invention.

Referring to FIGS. 15 and 16, the system (1410) of the present invention may be at least partially incorporated into a patient support. For example, referring to FIG. 15, a patient support 1402, such as a mattress may incorporate a drug delivery system 1410 of the present invention, which is embedded in the patient support surface, such as a mattress. System 1410 includes a chamber 1412 with a patient facing opening 1416 so that when a patient is placed on the patient support 1402 and the patient is resting on the patient support surface or mattress 1404, the weight of the patient's body will seal against the patient face opening 1416 to thereby seal the chamber against the patient's skin and thereby provide a sealed chamber (FIG. 15A). Similar to the previous embodiments, the chamber is optimally pressurized through a conduit 1422, which may also direct a drug, as a gas, and/or moisture to the chamber, in a similar manner described in reference to the previous embodiments. Alternately, as noted in reference to the previous embodiments, a drug may be topically applied to the patient's tissue prior to placement over the mattress and over the chamber with the chamber pressurized to facilitate the absorption of the drug into the patient's body through the patient's tissue.

Referring to FIG. 16, a patient support 1502 in the form of a chair is illustrated, which incorporates multiple drug delivery systems 1510 with one located in the back seat section of the chair and two incorporated into the seat section of the chair. As would be understood from the previous embodiment, each drug delivery system includes a patient facing opening 1516, which is in fluid communication with the chamber (1512) of the respective drug delivery system 1510. In this manner, when a patient is seated in chair 1502, the patient's weight will cause the patient's skin to seal against the patient facing opening(s) 1516 to thereby create a sealed chamber for treatment of the patient as described in reference to the previous embodiment. Systems 1510 may be independently controlled or may be controlled by a single control system, in which case the control system may be configured to independently pressurize each chamber and deliver different treatments to each chamber.

Figure 17:
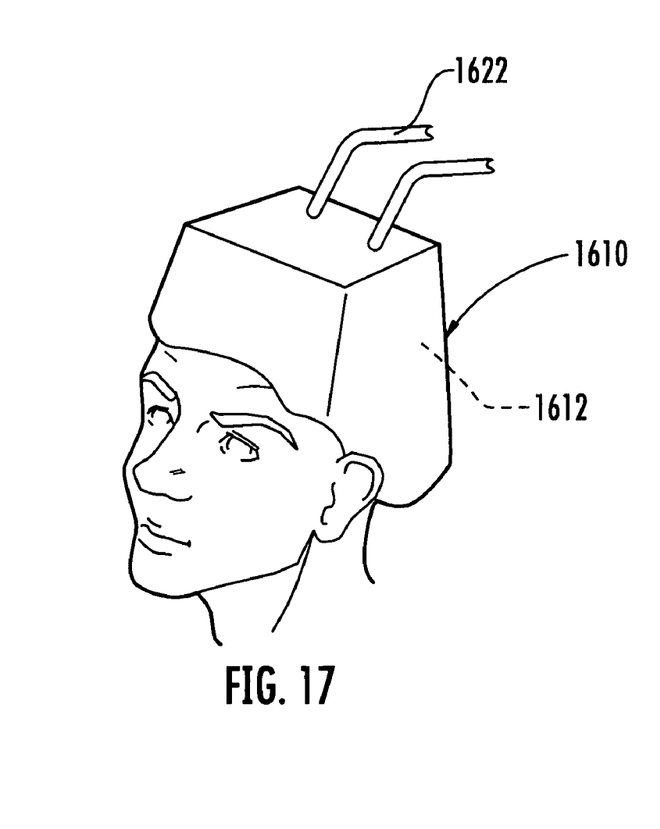
FIG. 17 is another embodiment of a chamber of the present invention, which is adapted to extend over at least a portion of a patient's head.
Figures 18A, 18B:
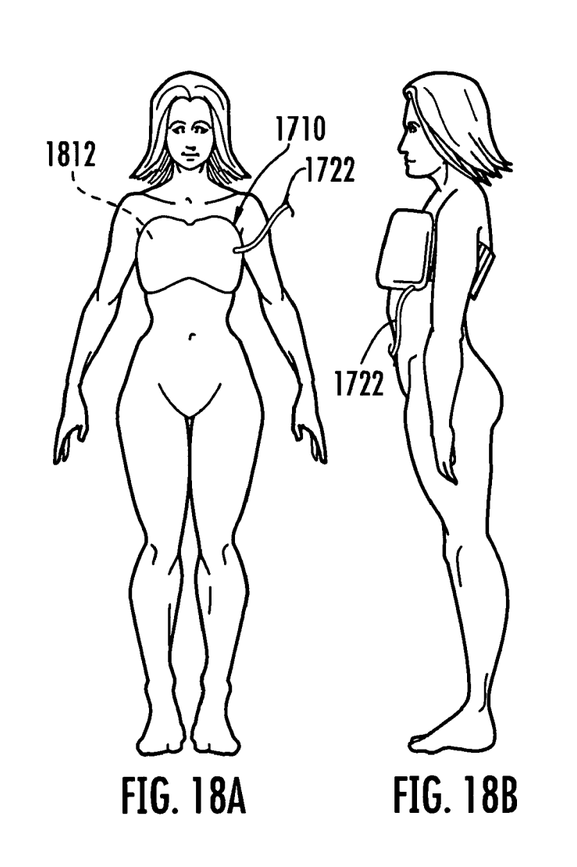
FIG. 18A is a front elevation view of a female patient with another embodiment of the chamber of the drug delivery system of the present invention for delivering a drug to the patient's breasts.
FIG. 18B is a side elevation view of the patient and chamber of FIG. 18A.

Referring to FIG. 17, the numeral 1610 generally designates another embodiment of a drug delivery system of the present invention, which is configured for covering and treating a head of a patient. In this illustrated embodiment, drug delivery system 1610 includes a chamber 1612, which is configured to cover a scalp of a patient for treating the scalp, for example for delivery of a drug that may, for example promote hair growth. As would be understood from the foregoing description, conduit 1622 is in fluid communication with chamber 1612 for delivering a drug, a gas, and/or moisture, as well as pressure, to chamber 1612 to thereby pressurize chamber 1612 and, further, to allow the drug to be applied to the patient's scalp under pressure. Alternately, as previously noted, the drug may be applied directly to the skin of the patient with the chamber placed over the patient's scalp to apply pressure and/or gas to the patient's scalp to enhance absorption of the drug in the patient's skin.

Referring to FIGS. 18A, 18B, 19A, and 19B, as noted previously, the drug delivery system of the present invention may be configured to treat targeted areas of the body including, for example, the chest of a patient. For example, drug delivery system 1710 includes a chamber 1712 that is configured for covering and treating a woman's breasts, for example for breast size enhancement or for post operative treatment. For example, medications may be applied using drug delivery system 1710 in a manner similarly described in reference to the previous embodiments, with the drug applied directly to the skin of the patient or applied in the form of a gas or liquid using system 1710. Alternately or in addition, system 1710 may be used to apply pressurized oxygen to a woman's chest to minimize post surgical augmentation or mastectomy scarring.

Figure 19A:
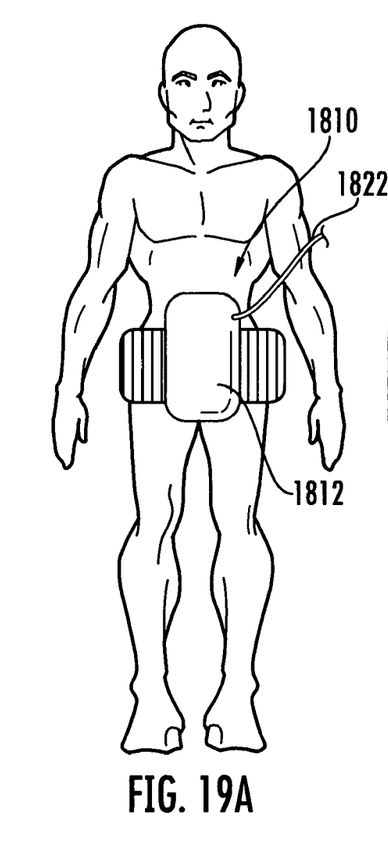
FIG. 19A is a front elevation view of yet another embodiment of the chamber of the present invention that is configured for delivering a drug to the groin area of a male patient.
Figure 19B:
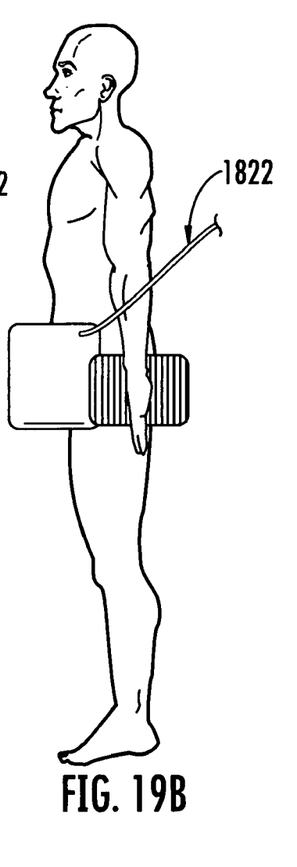
FIG. 19B is a side elevation view of the patient and chamber of FIG. 19A.

Referring to FIGS. 19A and 19B, drug delivery system 1810 includes a chamber 1812 that is configured to cover and treat male organs. For example, system 1810 may be adapted to deliver and apply erectile dysfunction (ED) medications. Similarly, system 1810 may also be used to apply ED medications in combination with negative pressure therapy for enhancement of the male organ size. By localizing the application of the medication, the drug delivery system of the present invention avoids systemic complications.

Figure 20:
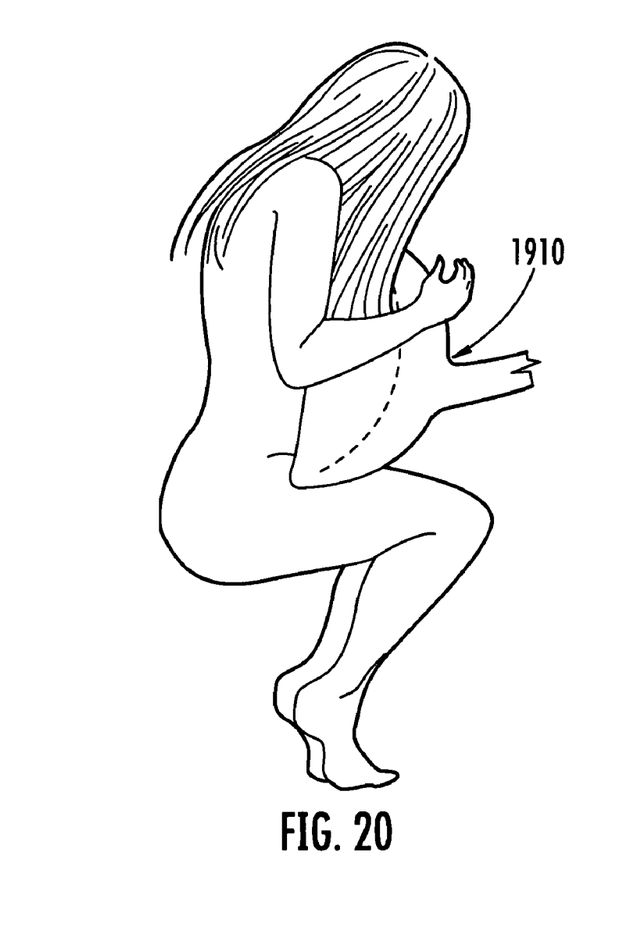
FIG. 20 is a side elevation view of a female patient being treated with another embodiment of the chamber of the drug delivery system of the present invention.
Figure 21:
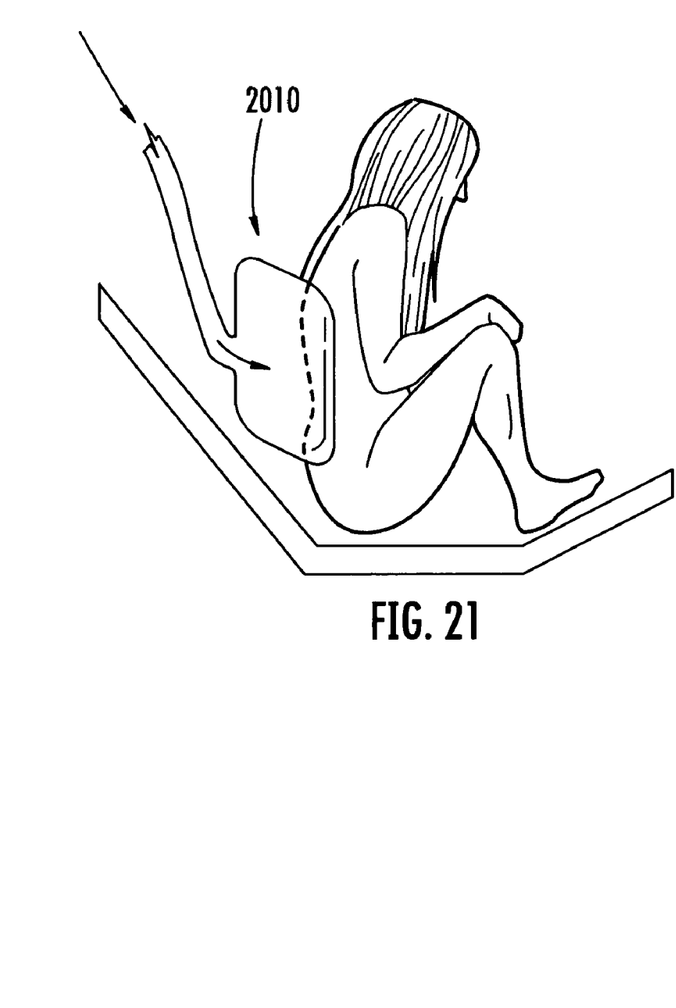
FIG. 21 is a side elevation view of a female maternity patient being treated with yet another embodiment of the chamber of the present invention.

Referring to FIGS. 20 and 21, chambers 1912 and 2012 of drug delivery systems 1910 and 2010 are specially configured to treat a pregnant woman. For example, drug delivery system 1910 may be used to deliver treatment to the unborn child via amniotic fluid and is, therefore, includes a chamber 1912 that is configured to envelope and cover the pregnant woman's extended abdomen. System 2010 includes a chamber 2012 that is configured to treat the back of the pregnant women, for example to administer pain relieving drugs to the pregnant woman's spine to reduce labor pain.

Figure 22:
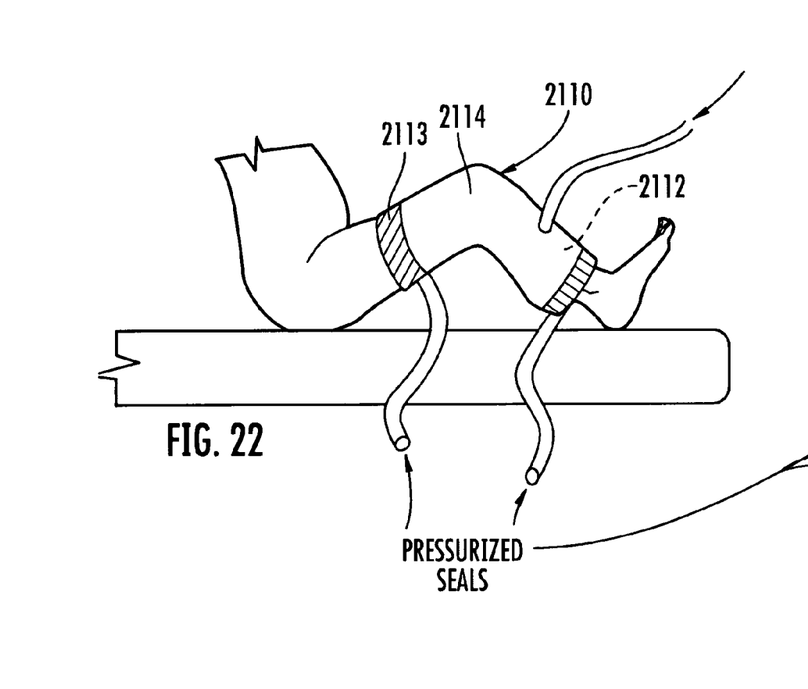
FIG. 22 is a schematic drawing of another embodiment of the chamber of the present invention in the form of a sleeve that incorporates pressurized cuffs.
Figure 23:
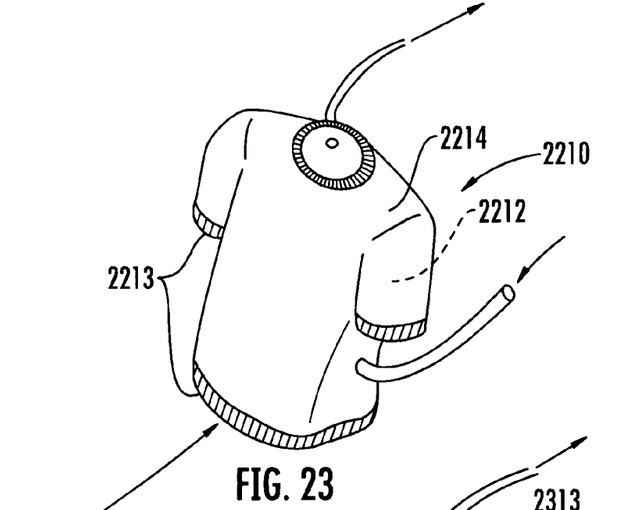
FIG. 23 is a schematic drawing of a chamber configured as a garment that covers the upper body of a patient and which incorporates a plurality of pressurized cuffs.
Figure 24:
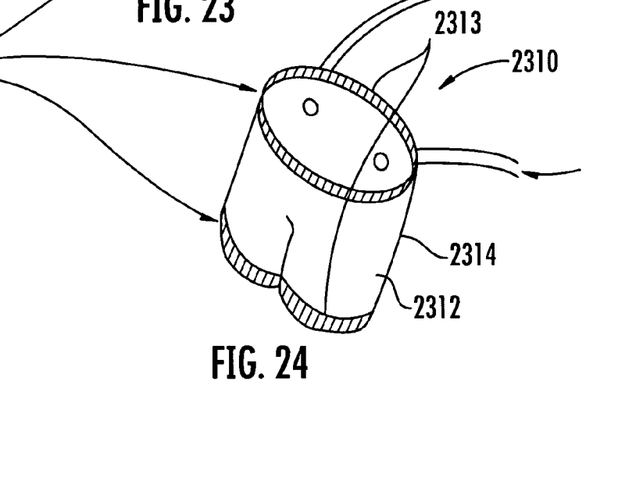
FIG. 24 is a schematic drawing of yet another embodiment of a chamber of the present invention configured as a garment, which also incorporates pressurized cuffs.

Referring to FIGS. 22-24, the housings 2114, 2214, and 2314 of drug delivery systems 2110, 2210, and 2310 of present invention may also be configured in the form of garments that may be worn by a patient. For example, housing 2114 is configured in the form of a sleeve, such as a leg sleeve. Housing 2214 is in the form of a shirt. Housing 2314 is in the form of a pair of shorts. In each case, the garment forms the chambers (2112, 2212, and 2312), which are constructed of flexible but generally airtight fabric and are sealed against the patient's body by inflatable cuffs (2113, 2213, 2313) to thereby seal the respective chambers. Again, conduits 2122, 2222, 2322 are provided that are in fluid communication with the respective chambers to deliver pressure to the chambers and optionally the drug, gas, and or moisture or mixtures thereof. Further, the respective control systems may control the pressure in the respective cuffs (2113, 2213, and 2313) to optionally vary the pressure in the cuffs to provide Deep Vein Thrombosis (DVT) therapy as well.

For further details of the various optional components and methods of treatment of drug delivery systems 310-2310, reference is made to drug delivery systems 10 and 110. In addition, any one of the chambers described herein may be used in conjunction with a pulsed lavage treatment or debridement treatment. For example, an access port may be provided that allows the tip of a lavage or debridement device to be inserted into the chamber. Thus, when administering a drug to a wound, enhanced treatment may be achieved when combined with cleansing of the wound bed, such as by lavage or debridement. For example of suitable devices for lavage or debridement treatment reference is made hereinto U.S. Pat. Nos. 4,278,078; 5,810,770; 6,471,668; 6,179,807, 6,6652, 488; 6,371,934; 6,099,494; and 7,153,287, which are all commonly owned by Stryker Corporation of Kalamazoo, Mich. and which are incorporated by reference in their entireties herein. Further, any one of the chambers described herein may be used to treat dermatological condition, including the translocation of enzymes, antibiotics, drugs and regulatory molecules for the treatment of baldness, cellulite, infections, scar tissue and other skin disorders. Further, the chamber may be used to apply a vacuum to extract or remove, for example, dyes or other fluids from a patient's body.

Accordingly, the present invention provides a drug delivery system that may enhance absorption of a drug containing liquids or creams that are applied directly to the patient's tissue, such as skin, by pressurizing the patient's tissue. Alternately, the drug may be directed to the patient's tissue in a gas, vapor, or liquid form, or combination thereof, which is delivered in a pressurized chamber to thereby enhance the through-the-surface-tissue absorption of the drug by the patient. Consequently, the present invention eliminates the need for injection or suppository use. Further, multiple drugs may be delivered simultaneously or sequentially, which may minimize drug-to-drug interaction associated with oral dosage forms of the drug.

While several forms of the invention have been shown and described, other forms will now be apparent to those skilled in the art. As noted above, the present invention may be used to treat a variety of conditions, including the treatment of wounds, alleviation of pain, treatment of dermatological conditions, including baldness, cellulite, infections, scar tissue and other skin disorders.

For example, features of one embodiment may be combined with features of another embodiment. Therefore, it will be understood that the embodiments shown in the drawings and described above are merely for illustrative purposes, and are not intended to limit the scope of the invention which is defined by the claims which follow as interpreted under the principles of patent law including the doctrine of equivalents.

The invention claimed is:

1. A method of applying a drug to a patient's skin surface to facilitate entry of the drug through the skin surface or tissue, the method comprising:

enclosing the skin surface, with a chamber, the chamber capable of being pressurized and maintaining a pressurized environment;

providing a drug;

exposing the skin surface or tissue of the patient to the drug;

pressurizing the chamber above ambient pressure and maintaining the pressure in the chamber above ambient pressure wherein the drug is administered to the surface or tissue of the patient under pressure; and facilitating entry of the drug through the skin surface or tissue by cycling the pressure between a positive first pressure above ambient pressure and a positive second pressure above ambient pressure, the first pressure being different than the second pressure to provide intermittent pressurization at said skin surface or tissue to thereby facilitate entry of the drug through the skin surface or tissue.

2. The method according to claim 1, further directing the drug into the chamber and controlling the flow of the drug into the chamber.

3. The method according to claim 1, further including directing a gas into the chamber.

4. The method according to claim 1, further comprising changing the humidity in the chamber.

5. The method according to claim 1, further comprising generating a spray or mist with the drug and directing the spray or mist into the chamber.

6. The method according to claim 5, further comprising controlling the flow of the spray or mist into the chamber.

7. The method according to claim 1, further comprising regulating the temperature of the drug being transferred to the chamber.

8. The method according to claim 1, further comprising enlarging the pores of the patient's skin.

9. The method according to claim 1, further comprising providing a patient support having a patient support surface, locating the chamber in the patient support, wherein the chamber has a patient-facing opening for facing a patient, and providing the patient-facing opening at the patient support surface wherein the weight of the patient seals the patient facing opening against the patient's skin.

10. The method according to claim 3, wherein said directing a gas includes directing a gas containing oxygen.

11. The method according to claim 1, further comprising applying a current to the skin of the patient.

12. The method according to claim 1, further comprising applying a voltage to the skin of the patient.

13. The method according to claim 1, further comprising applying an ultrasound wave to the skin surface of the patient.

14. The method according to claim 1, further comprising applying radiation to the skin surface of the patient.

15. The method according to claim 14, wherein said applying radiation comprises applying electromagnetic radiation, applying microwave radiation, or applying RF radiation.

16. The method according to claim 1, wherein said enclosing includes enclosing an appendage of the patient's body in the chamber.

17. The method according to claim 1, wherein said enclosing further includes immersing a portion of the patient's body with the surface in a liquid in the chamber.

18. The method according to claim 1, wherein the chamber is portable, said method further comprising mounting the chamber to the patient's body over the patient's skin surface or tissue to thereby enclose the patient's skin surface or tissue.

* * * * *